United States Patent
Chavana, Jr. et al.

(10) Patent No.: US 8,302,248 B2
(45) Date of Patent: Nov. 6, 2012

(54) HANDHELD VACUUM ATTACHMENT WITH ULTRAVIOLET LIGHT

(75) Inventors: Ernest Matthew Chavana, Jr., Cookeville, TN (US); Steven Wayne Myers, Buffalo Valley, TX (US)

(73) Assignee: Oreck Holdings LLC, Nashville, TN (US)

( * ) Notice: Subject to any disclaimer, the term of this patent is extended or adjusted under 35 U.S.C. 154(b) by 0 days.

(21) Appl. No.: 13/011,469

(22) Filed: Jan. 21, 2011

(65) Prior Publication Data
US 2011/0214686 A1 Sep. 8, 2011

Related U.S. Application Data

(60) Provisional application No. 61/311,684, filed on Mar. 8, 2010.

(51) Int. Cl.
*A47L 9/02* (2006.01)

(52) U.S. Cl. ............. 15/246.3; 15/319; 15/339; 15/344; 134/1; 134/21

(58) Field of Classification Search .................... 15/319, 15/339, 246.3, 344, 415.1; 134/1, 21
See application file for complete search history.

(56) References Cited

U.S. PATENT DOCUMENTS

| 6,148,474 A | 11/2000 | Ohara et al. |
| 7,507,980 B2 | 3/2009 | Garcia |
| 2010/0104471 A1* | 4/2010 | Harmon et al. ............... 422/24 |

FOREIGN PATENT DOCUMENTS

| EP | 1 731 073 A3 | 12/2006 |
| GB | 2 181 042 A | 4/1987 |

* cited by examiner

*Primary Examiner* — David Redding
(74) *Attorney, Agent, or Firm* — Winston & Strawn LLP (57) ABSTRACT

A vacuum cleaner attachment and a method of control of the vacuum cleaner attachment are described. The vacuum cleaner attachment comprises an ultraviolet light source to irradiate and disinfect various cleaning surfaces. Various embodiments of the attachment include one or more safety features concerning activation, enabling, and disabling of the ultraviolet light source based on various parameters such as distance between the attachment and a cleaning surface, time that such a distance is greater than a predetermined time period, and temperature of the ultraviolet light source in order to enable safe and effective operation of the attachment.

25 Claims, 6 Drawing Sheets

HANDHELD VACUUM ATTACHMENT WITH ULTRAVIOLET LIGHT

CROSS REFERENCE

This application claims the benefit of U.S. Provisional Patent Application No. 61/311,684, filed on Mar. 8, 2010, which is incorporated by reference in its entirety herein.

Applicants also incorporate by reference in its entirety co-filed U.S. patent application Ser. No. 13/011,500 entitled: "PORTABLE CANISTER VACUUM".

FIELD

The teachings herein generally relate to using ultraviolet radiation to disinfect various cleaning media. In particular, devices and processes that can be employed to disinfect or sanitize infestation agents within various cleaning media by using ultraviolet radiation are disclosed.

BACKGROUND

Many homes and businesses suffer from infestations of allergens and other undesirable organic and inorganic substances, such as molds, viruses, bacteria, and dust mites. Floor coverings such as carpeting in homes and hotels, for example, can contain a high concentration of organic or inorganic substances which create a potentially unhealthy or harmful environmental condition. A common indoor allergen in carpeting and mattresses that can trigger allergy symptoms in humans is the dust mite, a microscopic insect related to spiders. It has been claimed that allergies developed in the early years of a child's life due to exposure to allergens can result in life-long allergic responses or more serious medical conditions such as asthma. Exposure to mold spores, for example, has been linked to certain types of respiratory illnesses. Long term exposure to mold can cause asthma or other respiratory problems, even in individuals who are not naturally sensitive or allergic to mold.

Conventional cleaning methods do not effectively reduce populations of infestation agents present within carpeting. Standard vacuum cleaners do not sanitize or disinfect carpeting and vacuuming alone usually removes only a fraction of allergens from carpeting. Typically, steam cleaning is cumbersome, expensive, and can involve the use of chemicals. Also, steam cleaning can leave a carpet and its carpet pad in a wet condition that can support the undesirable growth of molds, mildew, bacteria, or dust mites in or beneath the carpet. As another alternative, chemical powders or dry carpet cleaning powders comprised primarily of chemical pesticides and insecticides can be used to clean carpeting. The potential health and safety hazards associated with such chemical powders, however, often outweigh any benefits that might be obtained by using them.

Many experts have suggested that the only solution to dealing with infestation agents in carpeting is to remove existing carpeting altogether and to refrain from using carpeting as a floor covering. However, for many individuals who find carpeting desirable, and for many applications where carpeting is an optimum choice for a floor covering, this is not an acceptable solution. As a result of the inadequacy of conventional carpet cleaning methods, however, carpeting in homes and commercial establishments can become an ideal environment in which dust mites, germs, bacteria, viruses, molds and other pathogens or microorganisms can live, grow, and multiply.

In addition, mattresses and other like articles are often afflicted by infestation agents. By the nature of how a mattress is used for rest or sleep, it is frequently in close contact with humans or animals that can shed dead skin, for example, or discard other organic substances that are retained in the mattress. Insects such as dust mites can thrive on this organic matter and quickly develop into a significant population within the mattress. As described above for carpeting, conventional cleaning methods applied to a mattress cannot both safely and effectively reduce populations of infestation agents present within the mattress.

Prior art ultraviolet (UV) handheld units either do not use a proximity sensor to determine if UV light is irradiating a cleaning surface, or use a proximity sensor which disables the UV sensor immediately when a proximity sensor senses that the cleaning surface is too far away. The handheld UV unit without the proximity sensor can be dangerous for an unwary user. The other prior art handheld UV units can be very frustrating to use on uneven surfaces. Even more frustrating is that once disabled, a UV lamp may take two or more seconds to turn back on. This can be due to a safety feature or that an electrical ballast used in light most UV lamps can take that that much time to turn the UV bulb on. There exists a need for a handheld UV unit that uses a proximity sensor but which delays a disabling of the UV lamp for a predetermined time or when the distance between a cleaning surface and the UV lamp is less than a predetermined distance.

In view of the problems described above, safe and effective disinfecting devices are needed to address the deficiencies of conventional processes for sanitizing cleaning media such as carpeting and mattresses.

BRIEF DESCRIPTION OF THE FIGURES

The same reference number represents the same element on all drawings. It should be noted that the drawings are not necessarily to scale. The foregoing and other objects, aspects, and advantages are better understood from the following detailed description of a preferred embodiment with reference to the drawings, in which.

DETAILED DESCRIPTION OF PREFERRED EMBODIMENTS

The teachings provide embodiments of cleaning and/or disinfecting devices and methods, and features thereof, which offer various benefits. The devices and methods can employ multiple and integrated activation, enabling, and disabling safety mechanisms, systems, and steps that promote safe, efficient, and effective use of the devices and methods.

It has been discovered that UV light, particularly in the "C" spectrum ("UV-C"), can deactivate the DNA of bacteria, viruses, germs, molds, and other pathogens and microorganisms, thus destroying their ability to reproduce and multiply. The UV-C light has been used effectively in various applications to disinfect and sanitize hospital rooms, medical clinics, food production facilities, and drinking water. For example, U.S. Pat. No. 7,507,980, incorporated herein in its entirety by reference, discloses using UV-C light in an upright vacuum cleaner. However, existing products and processes have been unable to effectively and safely leverage the benefits of UV light to sanitize infestation agents in cleaning media such as carpeting and mattresses.

The devices and methods can employ a proximity sensor, timer, and/or a control circuit to enable and/or disable an ultraviolet light source when the distance between a point on the vacuum cleaner attachment and a cleaning surface ("a determined distance") is greater than a predetermined distance. A timer can be employed that measures the time period ("a measured time period") that the determined distance is greater than a predetermined distance and a control circuit can disable the ultraviolet light source when a measured time period that is greater than a predetermined time period to allow for safe, efficient, and effective use of the devices and methods.

The devices and methods can employ a control circuit that enables or disables an ultraviolet light source in response to a signal conveying the temperature of the ultraviolet light source, and where the control circuit can disable the ultraviolet light source until it reaches a predetermined temperature to allow for safe and efficient use of the devices and methods.

The devices and methods also maximize the disinfection capability of UV light by providing mechanisms for enhanced penetration of the UV light into a cleaning medium. The devices and methods offer various heat dissipation and air flow engineering features that can promote and maintain the safe and advantageous use of UV light sources, such as a UV light bulb, employed by the devices and methods. The devices and methods can employ multiple and integrated safety mechanisms and systems that promote safe and effective use of the devices and methods. As described below, embodiments of the device can be applied effectively for disinfecting infestation agents which reside in cleaning media such as carpeting and mattresses. Cleaning operations such as vacuum cleaning operations, for example, can also be performed in association with certain embodiments of the devices described herein.

As applied herein, the term "cleaning medium" includes any area, region, substrate, surface, or other medium that can be acted upon by UV light. Examples of "cleaning media" include, without limitation, carpets, mattresses, furniture, drapery, or other surfaces or media (e.g., hardwood, linoleum, and ceramic tile). A "cleaning surface" includes any surface of a cleaning medium that can be acted upon by UV light. The cleaning surface can be horizontal, as in a typical floor or mattress top surface, or vertical or at any other angle, such as with drapery and furniture surfaces. The term "carpet" as used herein includes all floor coverings having fibers, whether looped, tufted, hooked, needlefelt, woven or of other design, indoor or outdoor, of natural or synthetic materials, wall-to-wall or roll goods.

The term "infestation agent" can include any organism, microorganism, contagion, pathogen, germ, insect, and/or any other organic or inorganic substance which can be affected by application of ultraviolet radiation, or which can be present on or within a cleaning medium. Examples of "infestation agents" include, without limitation, viruses, bacteria, dust mites, molds, roaches, fleas, bed bugs, spiders, and other insects.

With reference to FIGS. 1 through 4, various embodiments can be provided in association with a disinfecting device (e.g., vacuum cleaner attachment 100). Device 100 can be structured to combine the functional or structural features of a standard vacuum cleaner attachment in conjunction with an ultraviolet light disinfecting apparatus, for example, UV light bulb 142C. In certain embodiments, vacuum cleaner attachment 100 can be structured for use as a combination cleaning and disinfecting device, in which both a disinfecting operation and a vacuum cleaning operation are performed. For example, vacuum cleaner attachment 100 can be attached to a vacuum cleaner via attachment hose 191 to provide suction that draws air and dirt from a cleaning surface through air duct 211 and semi-cylindrical cavity 210 (shown in FIG. 2). An optional agitator, such as brush 110, could be added to agitate a cleaning surface and thus improve cleaning.

Figure 1:
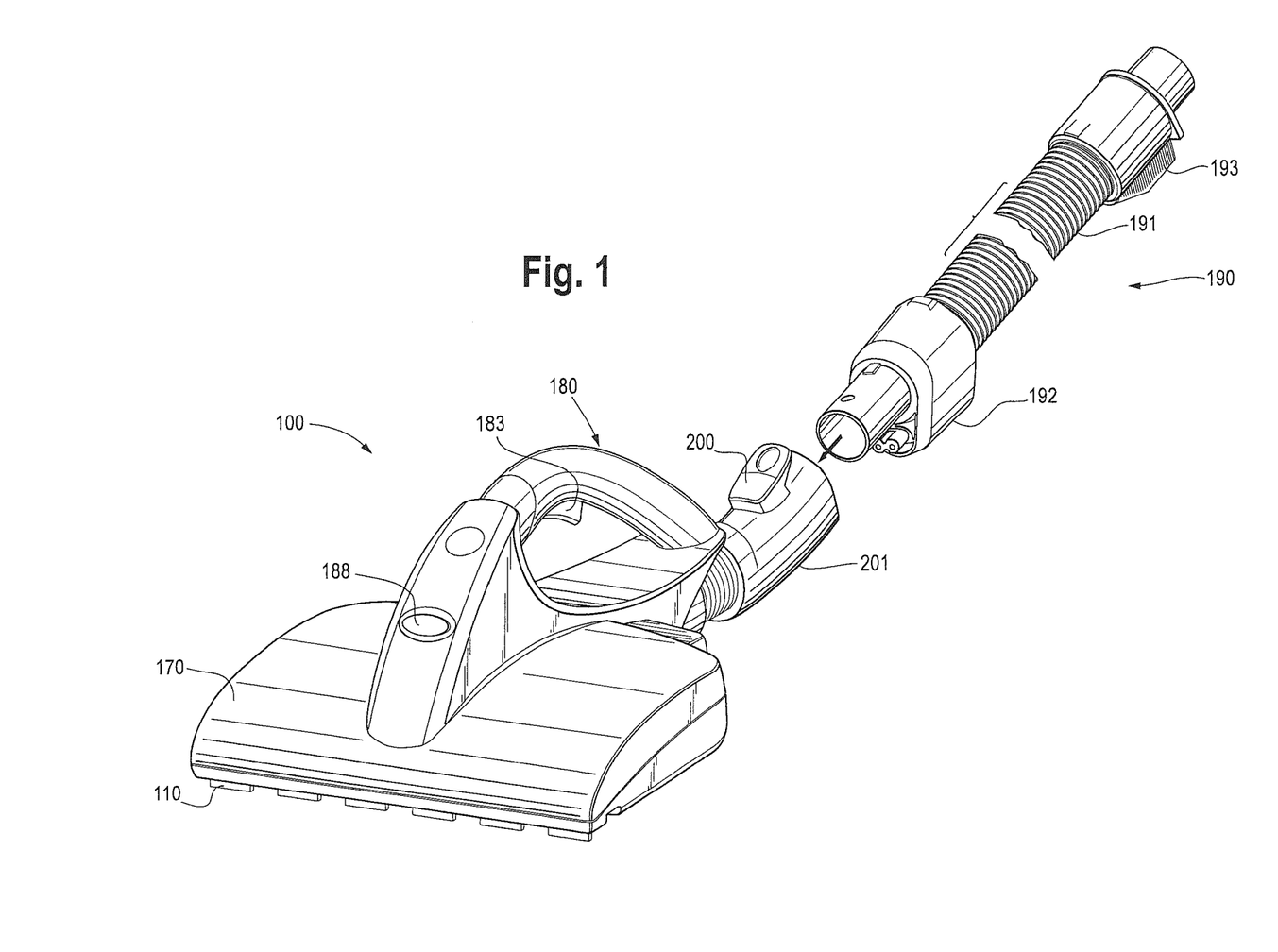
FIG. 1 is a perspective view of a handheld vacuum attachment in accordance with an embodiment.
Figure 2:
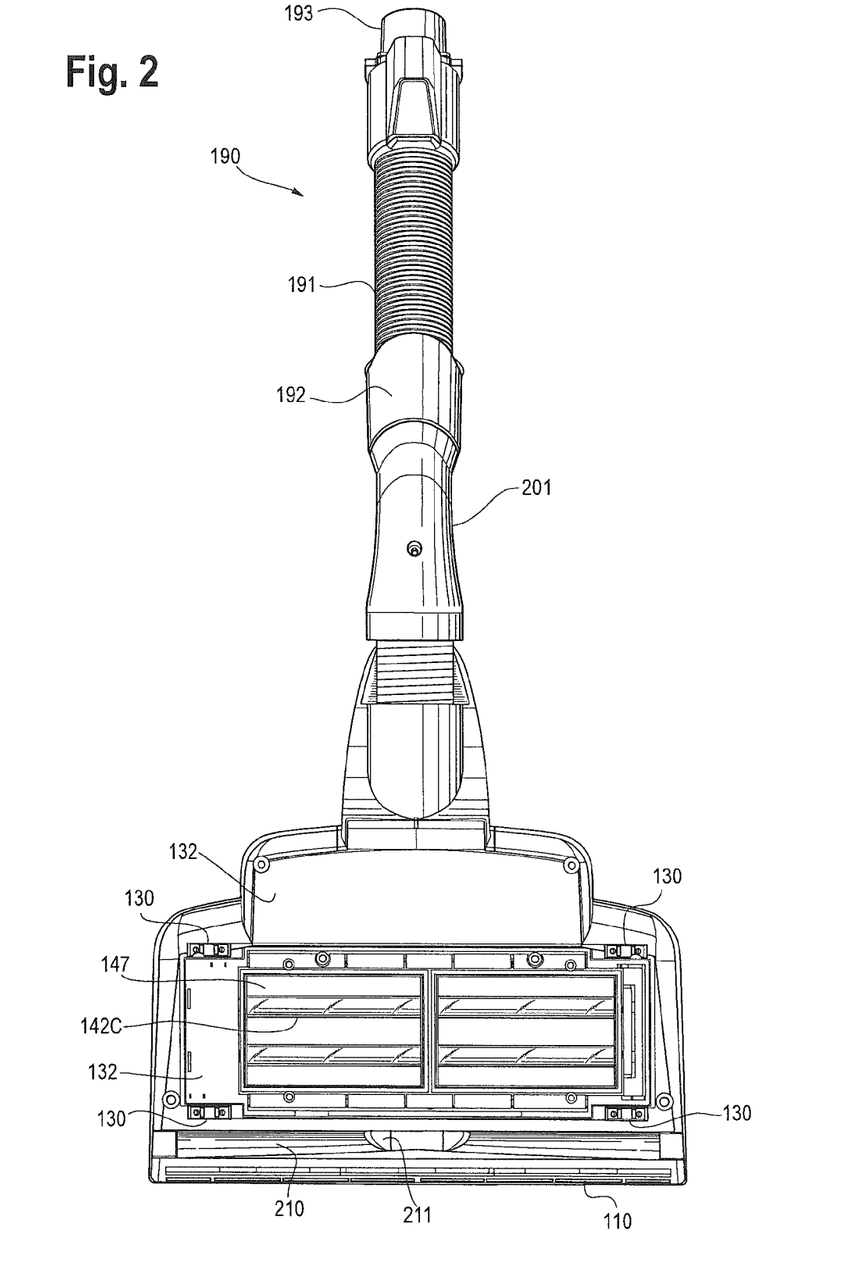
FIG. 2 is a bottom view of a handheld vacuum attachment in accordance with an embodiment.

In various embodiments, an optional beater bar (not illustrated) can be added within semi-cylindrical cavity 210 to provide additional agitation of the cleaning surface and improve cleaning. The beater bar can be configured to rotate during a beater bar operational mode of the device 100. The beater bar can be operatively associated with a beater bar motor, such as through a belt drive, to enable its rotation. The beater bar motor can be a single or variable speed motor of AC or DC variety that powers the rotation of the beater bar through a mechanical operative association with the belt drive. It can be appreciated that the beater bar can be configured to rotate with sufficient speed to effectively impact the cleaning surface on which the device 100 is employed. For example, the beater bar and beater bar motor can be selected or configured so that carpet fibers can be effectively agitated on both higher and lower nap carpeting. In other embodiments, the beater bar can be configured for effective sweeping of hard floor surfaces, mattresses, and/or furniture.

In various operational modes of device 100, the rotating beater bar or brush 110 can be structured to extract and carry infestation agents present within a cleaning medium to a surface of the medium and/or to within proximity of various portions of the base of the UV light source assembly 142.

In various embodiments, device 100 can be structured to perform disinfecting operations, with or without the additional capability to perform vacuum cleaning operations. Further, device 100 can be configured to selectively or jointly perform disinfecting and vacuum cleaning operations.

In another embodiment, device 100 includes a hose attachment port 201 with a locking mechanism 200 that permits connection of device 100 to attachment hose 190. Attachment hose 190 can comprise a flexible or rigid hose. Attachment hose 190 can comprise hose connection ports 192 and 193. Attachment hose 190 can supply electrical power to device 100. For example, attachment hose 190 can comprise an electrical wire. Such a device is described in U.S. Provisional patent application Ser. No. 61/311,684, filed Mar. 8, 2010. In some embodiments, the device can be used standalone. In a standalone, the device can be powered by a power cord when not attached to a vacuum cleaner.

In another embodiment, vacuum cleaner attachment 100 includes a handle 180 that allows a user to apply vacuum cleaner attachment 100 to a cleaning surface. A trigger 183 that allows a user to manually activate or deactivate ultraviolet light source 142C can be provided. Trigger 183 can be disposed in handle 180. An indicator 188 can be lit when ultraviolet light source 142C is radiating. Indicator 188 can be off when the ultraviolet light source 1420 is not radiating, for example, when the user manually deactivates the trigger or when ultraviolet light source 142C is disabled by a control circuit 140. Optionally, indicator 188 can flash when ultraviolet light source 142C is overheated or otherwise non-operational.

In another embodiment, control circuit 140 (FIG. 4) can enable or disable the ultraviolet light source 142C in response to one or more signals received from a proximity sensor 130, a timer, and/or a temperature sensor 142 that produces a signal conveying the temperature of the ultraviolet light source. In one embodiment, proximity sensor 130 determines the distance between a point on the vacuum cleaner attachment and the cleaning surface ("a determined distance"). In another embodiment, control board 140 determines the distance based on the signal from proximity sensor 130. In some embodiments, a timer measures the time period that the determined distance is greater than a predetermined distance. Control circuit 140 can comprise the timer. Control circuit 140 receives the distance signal from proximity sensor 130. Control circuit 140 can compute, determine or measure a time period based upon a timer. Control circuit 140 can disable ultraviolet light source 142C when the measured time period is greater than a predetermined time period.

The predetermined distance can be any length that allows for the UV light bulb to safely and effectively irradiate a cleaning surface. For example, the predetermined distance can be set at a length less than or equal to about one centimeter, such as 0.25 cm, 0.5 cm, 0.75 cm, or 1.0 cm. In another embodiment, the predetermined distance can be set to a distance of up to 10 cm or even up to 20 cm or more. A lower predetermined distance will increase the safety of the vacuum cleaner attachment, while the a larger predetermined distance will allow for irregular surfaces and smaller objects to be irradiated without the control circuit disabling a ultraviolet light source 142C.

In another embodiment, the predetermined time period is less than or equal to about one second, less than or equal to about five seconds, or less than or equal to about ten seconds. In a preferred embodiment, the predetermined time period is greater than zero, for example, about 10 milliseconds (ms), about 100 ms, about 200 ms.

In yet another embodiment, ultraviolet light source 142C is enabled when the determined distance is less than a predetermined distance. In another embodiment, control circuit 140 enables the ultraviolet light source after it has disabled the ultraviolet light source due to excessive temperature (e.g., greater than or equal to 85° C.) when the measured temperature of the ultraviolet light source is lower than a predetermined temperature (e.g., less than 40° C.).

In various further embodiments, vacuum cleaner attachment 100 comprises a housing 120 to which a variety of fascia 170 can be removably or permanently fastened.

Figure 5:
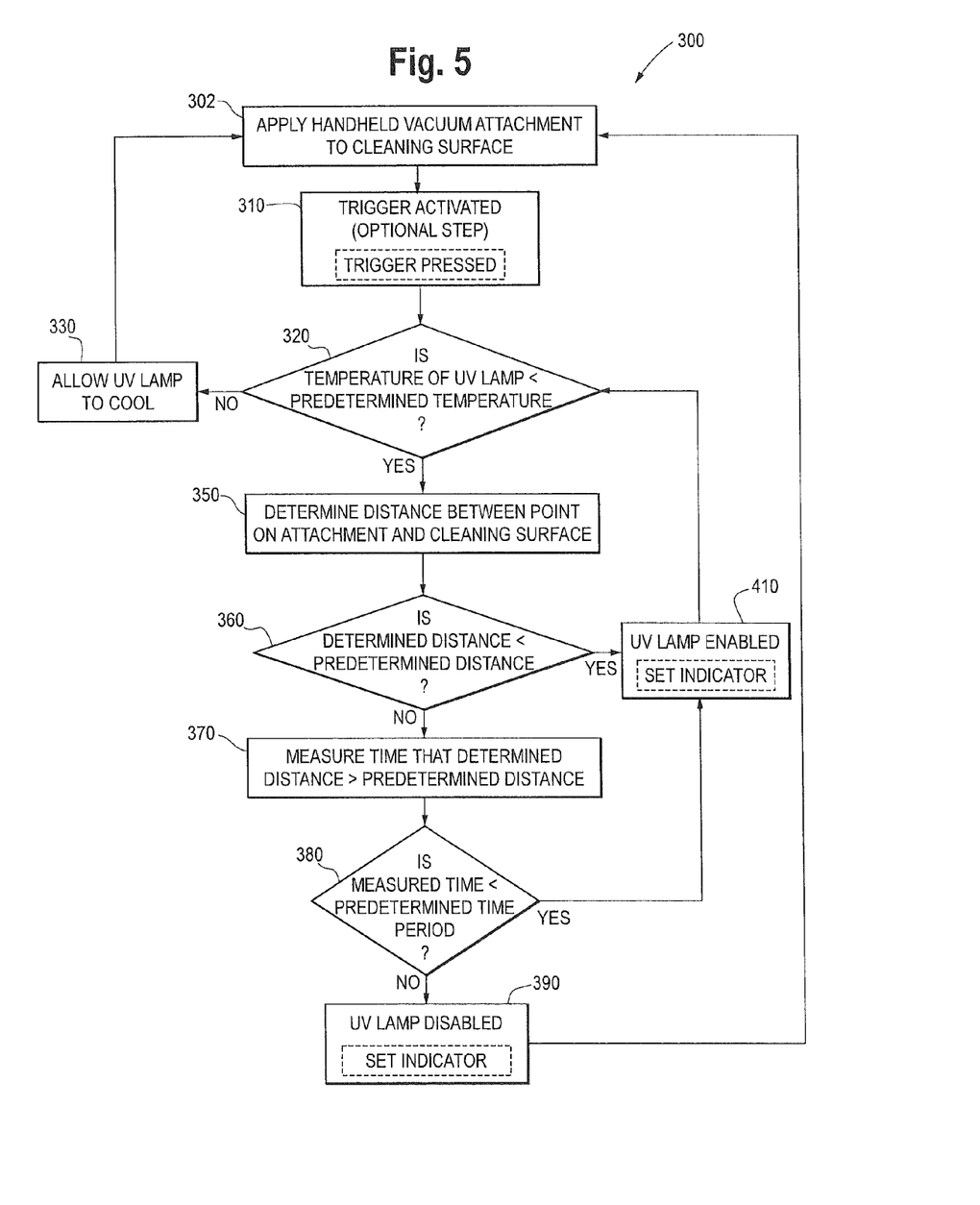
FIG. 5 is a process flow diagram of a method of cleaning a surface with a vacuum cleaner attachment in accordance with an embodiment.

With regard to the process flow diagram of FIG. 5, various methods of cleaning a surface with a vacuum cleaner attachment are contemplated. Method 302 discloses methods of operation and construction of a UV light source that includes a number of safety activation, enabling, and disabling steps. In one embodiment, in step 300 the vacuum cleaner attachment is applied to a cleaning surface. In step 310, a trigger can be activated by a user. When a trigger depression or activation is detected, step 320 determines if the temperature of a UV lamp is less than a predetermined temperature. Then, in step 350, a distance between a point on the vacuum cleaner attachment and the cleaning surface is determined. In step 360, when the determined distance is less than a predetermined distance the lamp is enabled per step 410. In step 360, when the determined distance is greater than or equal to a predetermined distance, the method continues to step 370. In step 370, the time period during which the distance determined is greater than the predetermined distance is measured. Per step 380, while the time period during which the distance is greater is less than a predetermined time period, the UV lamp is enabled per step 410. However, in step 380, when the time period during which the distance is greater is greater than the predetermined time period, the UV lamp is disabled per step 390. When a UV lamp is enabled, an indicator can be set. When a UV lamp is disabled because the cleaning surface is too far an indicator to show the error can be set. When the temperature of the UV bulb is excessive, an indicator can be set. The method can optionally reset the measured time period to zero when the determined distance is less than or equal to the predetermined distance.

Various other embodiments of the cleaning method include one or more of the following steps: irradiating the cleaning surface with an ultraviolet light source 142C through an opening in the attachment surface 147; enabling the ultraviolet light source 1420 when the determined distance is less than a predetermined distance; activating the ultraviolet light source 142C by activating a trigger 183 on the vacuum cleaner attachment 100; determining a temperature of the ultraviolet light source, and enabling or disabling the ultraviolet light source 142C in response to the determined temperature.

In another embodiment, the ultraviolet light source 142C is enabled when the determined temperature is less than 85° C. A further embodiment includes the step of cooling the ultraviolet light source 142C by drawing air over the ultraviolet light source 142C. A vacuum cleaner attached to vacuum cleaner attachment 100 can provide suction that draws air and dirt from a cleaning surface to semi-cylindrical cavity 210 through air duct 211 and to the vacuum cleaner via hose 191. In another embodiment, the cleaning method includes an optional step of agitating the cleaning surface with an agitator 110, such as a brush, and/or a beater bar that can be located within the semi-cylindrical cavity 210 in order to improve cleaning efficiency and effectiveness.

In another embodiment, the method includes applying an attachment surface of a vacuum cleaner attachment 100 to a cleaning surface; determining the distance between a plurality of points, such as four or more, on the vacuum cleaner attachment and the cleaning surface; measuring the time period that the determined distance for each plurality of points is greater than a predetermined distance; disabling the ultraviolet light source when the measured time period for any of the plurality of points is greater than a predetermined time period; and resetting a proximity sensor's time period to zero when its determined distance is less than or equal to a predetermined distance.

The embodiments described above include many benefits. First, the cleaning apparatus and method are completely chemical free. Instead of chemicals, germicidal ultraviolet light neutralizes many dust mite eggs, viruses, bacteria, mold, and other germs. This chemical-free cleaning apparatus and method eliminates the impact that many cleaning chemicals have on the environment. It improves user safety by reducing the risk of chemical ingestion, eye and skin irritation, respiratory irritation and other risks associated with using cleaning chemical. The absence of chemicals also eliminates the risk of chemical damage to cleaning surfaces, such as wood floors, carpets, furniture, cabinets, countertops, and other household items. Even with the use of chemicals, the disclosed cleaning apparatus and method provides broad protection against a wide range of contaminants to provide a healthier and cleaner environment.

In one embodiment, the vacuum attachment is attached to a vacuum cleaner. This combines the germicidal cleaning advantages of UV light with a powerful suction and traditional vacuum capability. When attached to a vacuum, the attachment can operate with UV light source 142C, suction from the vacuum via attachment hose 190, manual agitation using agitator 110, such as a brush, and powered agitation using a beater bar, either alone or in any combination. Thus, the cleaning apparatus and method includes a large number of different embodiments that each have unique advantages and provide a user with many options for cleaning any cleaning surface.

Exposure to germicidal ultraviolet light or touching the ultraviolet light during operation can result in burns and skin or vision damage. Accordingly, the cleaning apparatus and method includes a number of safety features to prevent personal injury or damage to cleaning surfaces. One should never stare directly at ultraviolet light. In order to prevent such an occurrence, the cleaning apparatus and method can include one or more optical sensors that measure the distance between a point on the vacuum and the cleaning surface.

A control circuit can disable the UV light if one or more of the sensors detect a distance that is greater than a predetermined distance. The predetermined distance could be preset from a manufacturer at a particular distance, such as 0.5, 1, or 2, inches. A user could have the option of setting the predetermined distance to any desired distance.

An optional timer can measure the time period for which an optical sensor determines a distance greater than a predetermined distance and disable the UV light when a measured time period is greater than a predetermined time period. The predetermined time period could be preset from a manufacturer at a particular time period, such as 1, 2, or 3 seconds. A user could have the option of setting the predetermined time period to a desired time period.

Alternatively, the vacuum can include a number of preset values for the predetermined distance and predetermined time period that a user could choose from depending on the type of cleaning surface being cleaned and the preferences of the user.

The attachment can optionally include a safety lock-out feature that disables the device or a portion of the device, such as the UV light, using any known lock-out mechanism, such as a lock and key, keypad and associated PIN code, combination lock, etc. in order to provide increased safety and childproof features.

The attachment includes a protective lens 147 to prevent a user from burning themselves or damaging a cleaning surface. In one embodiment, the attachment includes a safety feature to prevent such burning or damage that includes a temperature sensor that allows the UV light source 142C and protective lens 147 to cool down by disabling the UV light source 142C when the temperature exceeds a predetermined temperature, such as 85° C. The safety feature can allow the UV light source 142C to cool down to a temperature that is lower than a predetermined temperature, such as 40° C., before enabling the UV light source.

When the UV cleaner is used without continuous suction for an extended period of time, the cleaning apparatus and method can include a heat protection system that shuts off the UV light source 142C to avoid overheating and prevent permanent damage to the UV light source 142C and UV light assembly 142. An indicator can be included that can blink when the heat protection system shuts off the UV light source 142C. A control circuit can disable the UV light source 142C for at least 30 minutes for the UV-C bulb to cool and the system to reset.

Other safety features contemplated by various embodiments of the cleaning apparatus and method include: the unit must be on a flat surface to activate the UV-C light; the UV-C light will disengage if the product is raised off the flat surface or placed on a non-flat surface; keep the unit moving while in use; and a heat protection system.

In a method of operating the attachment, a user can place the attachment on a non-transparent/non-translucent surface, ensure that all safety sensors are in contact with the surface or up to predetermined distance, such as a ½ inch, off of the surface. The user can then plug in the power cord. Alternatively, power can be provided from an attached vacuum through the powered suction hose 190. A user can then activate the UV light source 142C by activating the activation switch 183, e.g. by squeezing and holding the activation switch 183. A user can then used UV light source to disinfect and clean cleaning surfaces. An indicator light can be illuminated to indicate that power is being supplied to the ultraviolet light. There can be a short delay before the ultraviolet light is activated.

The attachment can be operated with many canisters and vacuums with hose attachment openings by attaching the vacuum hose of the vacuum to attachment port 201 of the attachment 100, connecting its power cord and the vacuum/canister power cord into a power source, such as 120V/60 Hz socket, and turning the vacuum/canister on. A user can then vacuum at a steady speed and there is no need to exert pressure.

When using a vacuum that is compatible with powered hose 190, a user can insert the powered hose 190 into attachment port 201 until locking mechanism 200 secures the hose, such as when a click is heard. To remove the powered hose 190, a user can unlock locking mechanism 200, such as by depressing it, and pull the hose 190 out of the attachment port 201. A user can then unwind the necessary length of cord from the vacuum and insert the plug of the vacuum into a power source, such as 120V/60 Hz socket. A separate power cord for attachment 100 is not necessary when using powered hose 190. The user can then turn on the vacuum to power the attachment 100 and follow the same operating procedures disclosed for operating the UV light source of attachment 100. If the attachment is not kept close to a cleaning surface the attachment will automatically shut off.

The table estimates exposure times to neutralize many common microorganisms.

| Microorganism | Seconds for Kill |
|---|---|
| Virus | |
| Bacteriophage-*E. Coli* | 0.33 |
| Infectious Hepatitis | 0.40 |
| Influenza | 0.33 |
| Poliovirus | 0.33 |
| Bacteria | |
| *Bacillus anthracis*-Anthrax | 0.44 |
| *E. coli* | 0.33 |
| *Mycobacterium tuberculosis* | 0.50 |
| *Salmonella enteritidis* | 0.38 |
| Mold | |
| *Penicillium expansum* | 1.10 |

In various embodiments, a light bulb assembly 142 can be positioned within the attachment 104. As described below in more detail, the light bulb assembly 142 can be structured to radiate UV light onto or into a variety of cleaning surface upon which the device 100 can be employed. The UV light supplied by the light bulb assembly 142 can be configured to irradiate, sanitize, or otherwise disinfect a variety of infestation agents that can be present within a given cleaning surface. For example, the device 100 can use UV light radiated from the light bulb assembly 142 to sanitize dust mites living in the carpet flooring, mattresses, or furniture of a home or business.

In general, UV light wavelengths are considered less than about 400 nm and beyond the range of visible light. The UV portion of the light spectrum can be classified into three wavelength ranges: in the "A" spectrum UV-A (from 315 nm to 400 nm); in the "B" spectrum UV-B (from 280 nm to 315 nm); and, UV-C (from 100 nm to 280 nm). In general, UV light with a wavelength shorter than about 300 nm is considered effective at killing micro-organisms including bacteria, viruses, and molds. In particular, research has shown that UV-C light is optimal for killing micro-organisms. The UV-C range of light wavelengths is commonly called the "germicidal" bandwidth, because light in this range can deactivate the DNA of microorganisms and destroy their ability to multiply. Specifically, UV-C light causes damage to the nucleic acid of microorganisms by forming covalent bonds between certain adjacent bases in the DNA. The formation of such bonds prevents the DNA in the microorganism from being "unzipped" for replication, and the microorganism is unable to reproduce. When the microorganism tries to replicate, it is destroyed.

Dust mites often spend most of their time at or near the surface of cleaning media in which they are present, such as mattresses and carpeting, for example. Dust mite eggs and larvae can be at or near the surface, and/or deep within the cleaning media (e.g., buried in carpet fibers). UV-C light can be effective at disrupting the life cycle of microorganisms including dust mites, for example, if the UV-C light is shined directly on the eggs and larvae of the microorganisms. As a result, various embodiments can be structured to achieve maximum irradiation within a cleaning medium (e.g., within carpet fibers). This irradiation can be achieved by placing the UV light source (e.g., light bulb) above or near protruding members that condition the cleaning medium to receive penetrating UV-C light. The UV-C light has the potential to break the life cycle of various microorganisms such as dust mites, for example, by killing the embryonic stage and thereby stopping the production of allergenic proteins in feces and exuviae. It was found that even a relatively small dose of UV-C light had a fairly significant effect on dust mite reproduction, by affecting the rate of egg-laying and reproduction of the dust mites.

The effectiveness of UV light on infestation agents or microorganisms is directly related to the intensity of the light and exposure time. To be effective, the UV-C light rays can be directed to strike a microorganism with sufficient intensity and exposure time to penetrate the microorganism and break down its DNA molecular bonds. It is important to understand that UV light acts on a cumulative basis. In other words, if the molecular bonds of a particular microorganism are not broken down on a first application of UV light emanating from the device 100, subsequent applications of UV-C light will continue to break down the DNA on a cumulative basis with the prior applications. The dosage of UV-C light (in terms of millijoules per square centimeter or "$mJ/cm^2$") is a product of light intensity (or irradiance) and exposure time. Intensity is measured in microwatts per square centimeter ($\mu W/cm^2$), and time is measured in seconds. In a given region irradiated with UV-C light, for example, most microorganisms in the region can be eradicated with an efficiency of about four logs (that is, 99.99%) with a UV-C dosage of about 40 $mJ/cm^2$. For example, if it is assumed that the UV-C light intensity applied to a particular surface area of a cleaning medium is 2 $\mu W/cm^2$, and the exposure time is 20 seconds, then the UV-C light dosage would be 40 $mJ/cm^2$, thus eradicating or disinfecting about 99.99% of the microorganisms on the surface area. In numerous applications, UV-C radiation of about 253.7 nm can be useful for eradication or disinfection of various kinds of microorganisms, although the teachings are not limited to use at or near that range. In various embodiments, the disinfecting device can be configured to eradicate at least about 90%, or more preferably at least about 99% or 99.99%, of the infestation agents present within a cleaning medium during normal use.

Referring again to FIGS. 3A and 3B, the light bulb assembly 142 can include a frame 142A having a generally curved reflector 142B attached thereto which is structured to receive and at least partially enclose or encase an ultraviolet light bulb 142C therein. The reflector 142B can be composed of a reflective material (e.g., highly polished aluminum) that can serve to re-direct or reflect UV-C light emanating from the light bulb 142C toward the cleaning medium. The reflective surfaces can be smooth or faceted, specular or semi-specular, or diffusing and can be made of any reflective materials. The light bulb 142C can be, for example, a generally U-shaped, 35-watt, high-output, no-ozone bulb suitable for radiating light in the UV-C wavelength range of light. Alternately, a single linear bulb or multiple linear or shaped bulbs can be employed. The bulb 142C can be powered by insertion into a socket 142D which can be electrically connected to a ballast 150 or another power source. In certain embodiments, the ballast 150 can be a 120 VAC, 800 mA ballast, for example.

It can be appreciated that the intensity of radiation emitted from a UV light source (e.g., the light bulb 142C), and the associated disinfecting effectiveness of the radiation, are a function of the proximity of the UV light source to the cleaning medium. It has been found that, for certain applications and embodiments of the devices described herein, the light bulb 142C can be positioned no more than about 2 inches from a surface of the cleaning medium, more preferably no more than about 1 inch from the surface of the cleaning medium, and most preferably no more than about 0.5 inches from the surface of the cleaning medium, to maximize the effectiveness of the devices in disinfecting infestation agents present within a cleaning medium.

It can further be appreciated that the dosage of the UV radiation is a function of the time of exposure of the cleaning medium to the radiation. To this end, embodiments which provide for sufficient duration of exposure of the infestation agents to the UV radiation are described. Multiple UV bulbs can be employed, which when the device is in use, approximately double the amount of time the UV light irradiates any given area of cleaning medium over a single linear bulb design at a given rate of speed. Alternately, a U-shaped bulb can be employed, which can approximately double the exposure time over a single linear bulb at a given rate of travel. The device can employ multiple linear and/or shaped bulbs. Alternate arrangements such as one or more UV light emitting diodes can be employed as well.

The arrangement, shape and number of bulbs will effect the duration of exposure of the cleaning medium at a given rate of travel of the device. Obviously reaching a target dosage of 30-40 $mJ/cm^2$ is more easily achieved under normal use conditions if that dosage can be reached in 1-3 seconds of exposure. That is, a normal user is less likely to use the device slowly enough to expose the cleaning medium for a lengthy period of time, such as 20 seconds. The device is preferably designed such that at a normal rate of use, that is, at a normal or slow walking pace, any given area of cleaning medium will be exposed for a duration of time sufficient to eradicate 90% of infestation agents, or more preferably 99% or 99.99% of eradication. The arrangement of the bulb or bulbs can be designed to expose an area of cleaning medium, at a slow to normal walking pace, to at least one second of exposure to UV light and more preferably for about two seconds or more of exposure. The desired duration of exposure will vary depending on the intensity of the radiation as determined by the distance from the light source to the cleaning medium, the power of the light source and the effectiveness of reflectors.

Figure 3A:
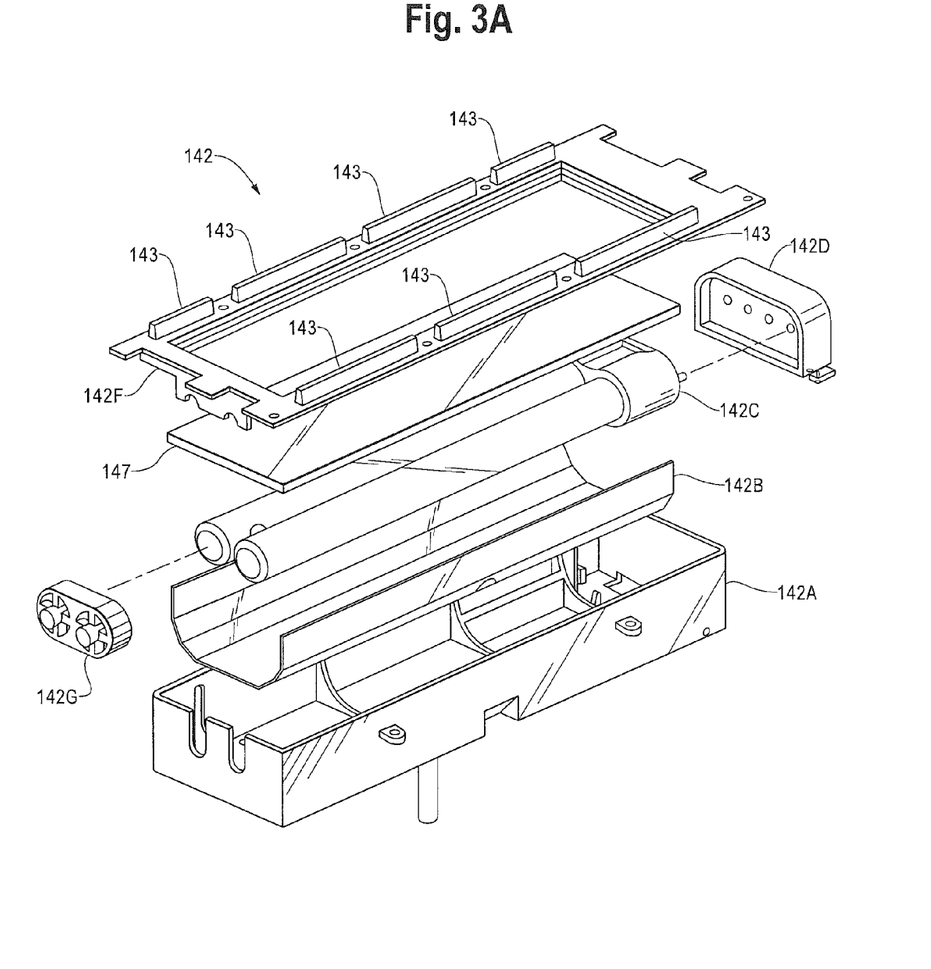
FIG. 3A is an exploded three-dimensional bottom-to-top view of an ultraviolet light source assembly of a handheld vacuum attachment in accordance with an embodiment.
Figure 3B:
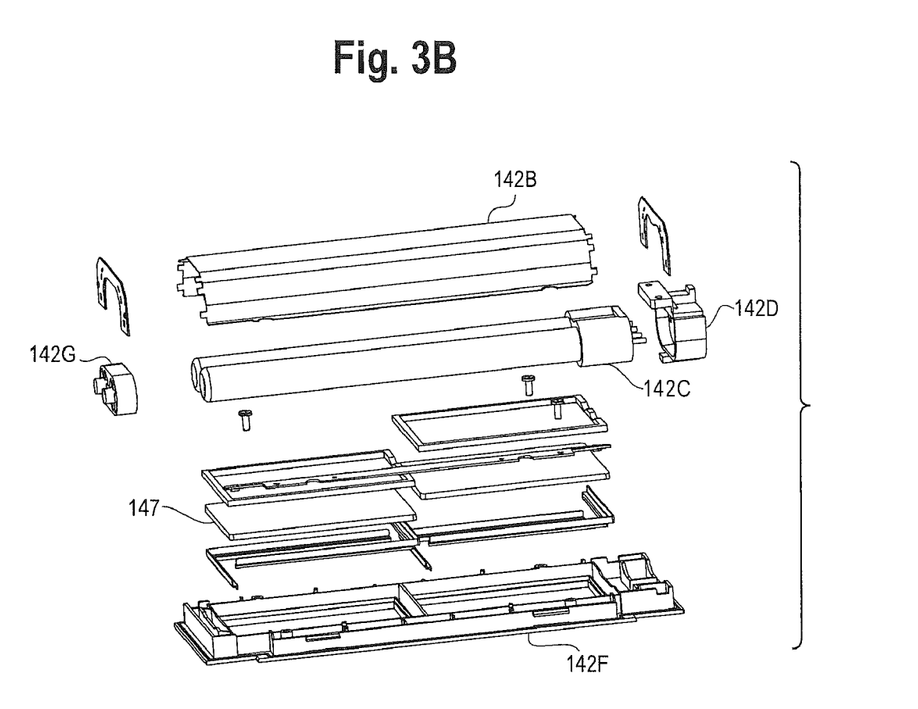
FIG. 3B is an exploded three-dimensional top-to-bottom view of an ultraviolet light source assembly of a handheld vacuum attachment in accordance with an embodiment.
Figure 4:
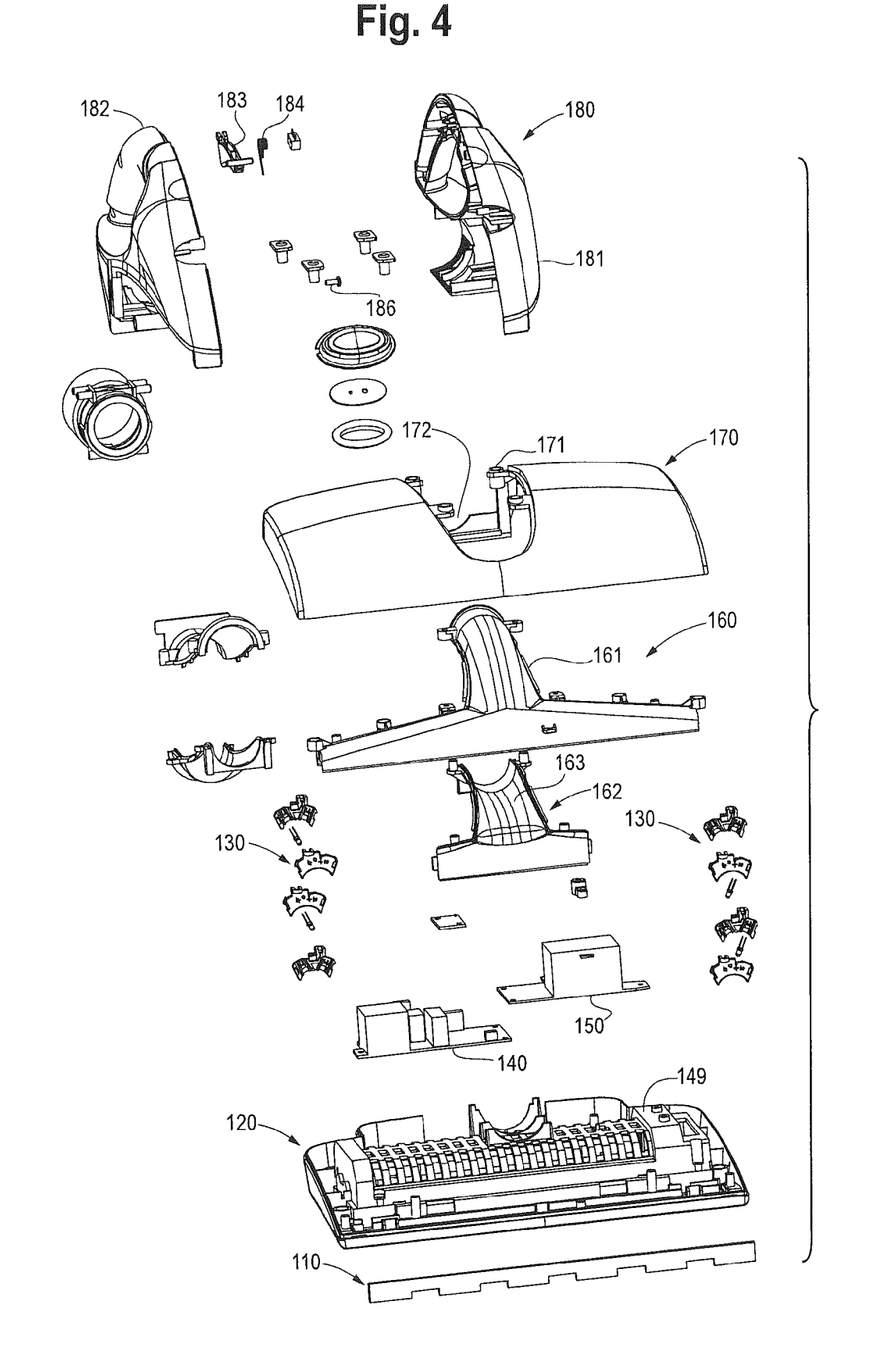
FIG. 4 is an exploded three-dimensional top-to-bottom view of a handheld vacuum attachment in accordance with an embodiment.

A lens 147 can be included in the light bulb assembly 142 positioned in a lens frame 142F, and this arrangement can serve to protect the light bulb 142C from breakage and/or direct contact with surfaces or other objects. To further protect the light bulb 142C from shock and vibration effects, an isolator 142G or shock absorber or dampener can be employed. The shock dampener can be made of rubber or another suitable material can be positioned on one or more if the distal ends of the light bulb 142C, as shown in FIG. 3A and FIG. 3B. In certain embodiments, foam or rubber cushions and/or suspension supports can be positioned adjacent to the light bulb 142C and/or around the socket 142D to absorb forces or vibration arising from operation and use of the device 100.

The lens 147 is preferably disposed between the light source or bulb 142C and the cleaning medium. The lens resists direct human contact with the light bulb 142O, which is advantageous because the presence of finger prints, for example, on the light bulb 142C can hinder transmittance of UV-C light during operation of the device 100. In the event the light bulb 142C breaks, for example, it can be seen that the lens 147 promotes containment of light bulb 142C fragments within the assembly 142. The lens 147 is made of a substantially translucent material. In certain embodiments, the lens 147 can be composed of a relatively thin (e.g., about 3 mm) fused silica or quartz glass, or a substance that allows greater than 80% transmittance of UV light therethrough. More preferably, the lens 147 allows greater than 90% transmittance of UV light, or 95% transmittance or higher. The thickness of the lens can vary, although typically the thinner the lens the better the transmittance. Accordingly, a thinner lens is preferable, in one embodiment a lens of no more then three mm is preferred.

Adjacent to the lens 147, or directly below the lens 147, at least one protruding member 143 extends from the device and into contact with the cleaning medium. Preferably the protruding members 143 extend from the lens frame 142F or from the lens 143 itself. During operation of the device 100, the protruding members 143 serve to act upon the cleaning medium (e.g., by contacting the medium and spreading open a section of carpet flooring or a mattress) to promote penetration of UV light into the cleaning medium. The protruding members 143 can also serve to prevent leakage reflection of UV light rays away from the interior of the light bulb assembly 142. Although a single protruding member can be employed, a plurality is preferred.

The protruding members 143 can be arranged variously, such as seen in FIGS. 3A and B. In FIG. 3A, the protruding members are arranged adjacent the lens 147, both in front of and behind the lens and UV light source 142C. Alternately, as seen in FIG. 3B, the protruding members can extend in front of the lens and UV light source 142C. The protruding members 143 can extend across the lens 147 longitudinally, diagonally, laterally, or any other desired configuration. Preferably, the protruding members are attached to the lens frame 142F, as seen in FIGS. 3A and B. Alternately, the protruding members can extend directly from the lens itself. For example, the lens 147 can be manufactured to include protruding members 143 therefrom or such members can be attached to the lens by adhesives and the like. The protruding members 143 can be opaque, translucent or transparent and can be made of rubber, plastic or other materials. Alternately the members 143 can be made of a plurality of bristles. The members 143 can be flexible or inflexible, but should be stiff enough to effectively move carpet fibers. If the protruding members extend across the direct path of the UV light, it can be preferable that they transmit UV light through to the cleaning medium.

The protruding members 143 can at least partially fall in the direct path of UV light irradiated form the UV light source 142C. The protruding members 143 are designed to contact a carpet cleaning medium, pushing the fibers of the carpet apart to create space for the direct shining of UV light upon areas of the fibers that would not otherwise receive direct radiation. As the device 100 is moved back and forth over the carpet cleaning medium, the protruding members 143 act to open up the medium to direct UV light. In this manner, the deeper areas of the medium which can bear infestation agents, especially eggs, are subject to irradiation. Since the effect of UV radiation on infestation agents is cumulative, the protruding members are designed to allow a greater combined duration of exposure as the device is moved back and forth across the cleaning medium.

The protruding members 143 can be stationary, as seen in FIGS. 3A and B, or can be designed to move relative to the device 100. For example, in an embodiment employing a beater bar, the beaters of the beater bar serve as protruding members 143 since they fall in the path of the light source 142C. In such a case, the protruding members are not stationary, but move independently with respect to the light source.

The lens frame 142F can be removably or pivotally attached to the device housing, such as by latches or other known mechanisms so that the lens frame can be moved away from the lens to facilitate cleaning of the lens.

In another embodiment of the device, the lens 147 is not supported above the surface of the cleaning medium. Rather, the lens is designed to contact the medium as the device is moved across the medium surface. In such a way, the lens is constantly wiped during use, thereby removing any dust that can otherwise adhere to the exterior of the lens 147. Since UV light is absorbed so readily, dust build-up on the exterior of the lens will adversely effect the disinfecting capabilities of the device. Consequently, the lens can be cleaned between uses by the user or, in the present embodiment. Use of the device constitutes a method for removing dust from the lens.

Radiant energy or light beams emitted from the light bulb 142C shine directly or indirectly from the light bulb 142C onto and/or into a cleaning surface. Light beams incident on the reflector 142B can be reflected back from the reflector 142B toward the cleaning surface to further enhance the effectiveness of the light bulb assembly 142 in disinfecting or sanitizing infestation agents residing within the cleaning surface.

In various embodiments, heat transfer can be affected by exposure to cooling air flow through the device 100, such as air flow generated during a vacuum operation. It can be appreciated that operation of the light bulb 142C within the light bulb assembly 142 can generate heat in the ambient environment or air around the light bulb 142C. The temperature of the ambient environment within the assembly 142 can impact performance or effectiveness of the light bulb 142C. Thus, in certain embodiments, it is desirable to structure the assembly 142 and housing 120 from conductive material or materials that conduct heat from the bulb 142C and into contact with the airflow streaming through the device 100, such as during a vacuum operation. Examples of suitable conductive materials that can be used include aluminum, aluminum alloys, or other metals that can adequately conduct heat away from the UV light source 142 and assembly 142. In certain embodiments, the reflector 142B is comprised of material that is both a reflective and heat conductive material.

In general, embodiments of the device 100 and methods described herein can be structured to operate in various modes: such as UV light only, which can be useful for germicidal applications, or vacuum only, or UV light plus vacuum. In various embodiments, the device 100 can be configured for use primarily to perform disinfecting operations in association with UV light or UV-C light radiated from the light bulb 142C. For example, such disinfecting operations can be performed with the device 100 as described above, with or without an accompanying vacuum cleaning operation capability, and/or with or without activation of a beater bar.

It is to be understood that the figures and descriptions herein have been simplified to illustrate elements that are relevant for a clear understanding, while eliminating, for purposes of clarity, other elements. Those of ordinary skill in the art will recognize, however, that these and other elements can be desirable. However, because such elements are well known in the art, and because they do not facilitate a better understanding of the present teachings, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects, a single component can be replaced by multiple components, and multiple components can be replaced by a single component, to provide an element or structure or to perform a given function or functions. Except where such substitution would not be operative to practice certain embodiments, such substitution is considered within the scope of the present teachings.

The physical composition of various structural and functional components described herein can be comprised of different kinds of suitable materials. Examples of suitable materials that can be employed include, without limitation, polypropylene, polycarbonate, ABS plastic, polyethylene (e.g., HDPE), various elastomeric materials, and polytetrafluoroethylene ("PTFE").

The examples presented herein are intended to illustrate potential and specific implementations. It can be appreciated that the examples are intended primarily for purposes of illustration for those skilled in the art. The diagrams depicted herein are provided by way of example. There can be variations to these diagrams or the operations described herein without departing from the spirit of the invention. For instance, in certain cases, method steps or operations can be performed in differing order, or operations can be added, deleted or modified.

We claim:

1. A vacuum cleaner attachment for cleaning surfaces, the attachment comprising:
   an ultraviolet light source to irradiate a cleaning surface;
   a proximity sensor to generate a distance signal representing the distance between a point on the vacuum cleaner attachment and the cleaning surface;
   a timer to obtain a time period during which the determined distance is greater than a predetermined distance; and
   a control circuit
      to receive the distance signal,
      to determine a distance based on the distance signal,
      to compare the distance with a predetermined distance, and
      to measure a time period during which the determined distance is greater than a predetermined distance;
   wherein the control circuit disables the ultraviolet lamp when the time period is greater than a predetermined time period and the predetermined time period is greater than zero seconds.

2. The vacuum cleaner attachment of claim 1 wherein the control circuit resets the time period to zero when the distance is less than or equal to the predetermined distance.

3. The vacuum cleaner attachment of claim 1 wherein the ultraviolet light source is enabled when the determined distance is less than the predetermined distance.

4. The vacuum cleaner attachment of claim 1 further comprising a temperature signal to convey a temperature of the ultraviolet light source, wherein the control circuit receives the temperature signal and enables or disables the ultraviolet light source based on the temperature signal.

5. The vacuum cleaner attachment of claim 4 wherein the control circuit enables the ultraviolet light source after it has disabled the ultraviolet light source due to excessive temperature when the measured temperature of the ultraviolet light source is lower than a predetermined temperature.

6. The vacuum cleaner attachment of claim 5 wherein the excessive temperature is greater than or equal to 85° C.

7. The vacuum cleaner attachment of claim 4 wherein the control circuit enables the ultraviolet light source when the temperature is less than 40° C.

8. The vacuum cleaner attachment of claim 1 wherein the vacuum cleaner attachment further comprises:
   a housing for disposing the ultraviolet light source; and
   a fascia fastened to the housing to allow for customizing a look of the vacuum cleaner attachment.

9. The vacuum cleaner attachment of claim 1 wherein the predetermined time period is less than or equal to about one second.

10. The vacuum cleaner attachment of claim 1 wherein the predetermined distance is less than or equal to about one centimeter.

11. The vacuum cleaner attachment of claim 1 wherein the proximity sensor comprises a light emitting diode and an optical sensor.

12. The vacuum cleaner attachment of claim 1 further comprising a hose attachment port to attach a vacuum cleaner to.

13. The vacuum cleaner attachment of claim 1 further comprising a trigger to activate the ultraviolet light source.

14. The vacuum cleaner attachment of claim 1 wherein the proximity sensor comprises a plurality of proximity sensors that each generate a distance signal representing the distance between a point on the vacuum cleaner attachment and the cleaning surface, and the control circuit receives the distance signal from each of the plurality of proximity sensors, determines a distance based on the distance signals, compares the distances with a predetermined distance, and calculates a time period during which at least of the distances is greater than a predetermined distance.

15. The vacuum cleaner attachment of claim 14 wherein the control circuit disables the ultraviolet light source during the time when the time period for a majority of the plurality of proximity sensors is greater than a predetermined time period.

16. The vacuum cleaner attachment of claim 1 wherein the plurality of proximity sensors comprises four or more proximity sensors.

17. A method of cleaning a surface with a vacuum cleaner attachment comprising:
   irradiating a cleaning surface with an ultraviolet light;
   determining a distance between a point on the vacuum cleaner attachment and the cleaning surface;
   measuring the time period that the distance determined by the proximity sensor is greater than a predetermined distance; and
   disabling the ultraviolet light source during the time when the measured time period is greater than a predetermined time period.

18. The method of claim 17 further comprising resetting the measured time period to zero when the determined distance is less than or equal to the predetermined distance.

19. The method of claim 17 further comprising enabling the ultraviolet light source when the determined distance is less than a predetermined distance.

20. The method of claim 17 further comprising enabling the ultraviolet light source by activating a trigger on the vacuum cleaner attachment.

21. The method of claim 17 further comprising:
   determining a temperature of the ultraviolet light source; and
   enabling or disabling the ultraviolet light source in response to the determined temperature.

22. The method of claim 21 wherein the ultraviolet light source is enabled when the determined temperature is less than 85° C.

23. The method of claim 17 further comprising cooling the ultraviolet light source by drawing air over the ultraviolet light source.

24. The method of claim 17 further comprising:
   determining the distance between a plurality of points on the vacuum cleaner attachment and the cleaning surface;
   measuring the time period that the determined distance for each plurality of points is greater than a predetermined distance; and
   disabling the ultraviolet light source when the measured time period for any of the plurality of points is greater than a predetermined time period.

25. The method of claim 24 wherein the plurality of points on the vacuum cleaner comprise four or more points on the vacuum cleaner attachment.

* * * * *